US00PP26875P2

(12) United States Plant Patent
Frangi

(10) Patent No.: US PP26,875 P2
(45) Date of Patent: Jun. 28, 2016

(54) ***LAGERSTROEMIA* PLANT NAMED 'MILAPERL'**

(50) Latin Name: *Lagerstroemia indica*
Varietal Denomination: Milaperl

(71) Applicant: Piero Frangi, Barlassina (IT)

(72) Inventor: Piero Frangi, Barlassina (IT)

(73) Assignee: Fondazione Minoprio, Como (IT)

( * ) Notice: Subject to any disclaimer, the term of this patent is extended or adjusted under 35 U.S.C. 154(b) by 76 days.

(21) Appl. No.: 14/544,053

(22) Filed: Nov. 19, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Mar. 17, 2016. p. 1.*

* cited by examiner

*Primary Examiner* — Annette Para
(74) *Attorney, Agent, or Firm* — Penny J. Aguirre

(57) ABSTRACT

A new cultivar of *Lagerstroemia indica* plant named 'Milaperl' that is characterized by its well-branched plant habit, its early and long lasting bloom period, its flowers that are pale pink in color, its good tolerance to powdery mildew, and its good frost resistance.

2 Drawing Sheets

Botanical classification: *Lagerstroemia indica.*
Variety denomination: 'Milaperl'.

CROSS REFERENCE TO RELATED APPLICATIONS

This application is co-pending with a U.S. Plant Patent Applications filed for plants derived from the Inventor's breeding program that are entitled *Lagerstroemia* Plant Named 'Milavio' (U.S. Plant patent application Ser. No. 14/544,052), 'Milarosa' (U.S. Plant patent application Ser. No. 14/544,050), 'Milarosso' (U.S. Plant patent application Ser. No. 14/544,051), and 'Milabla' (U.S. Plant patent application Ser. No. 14/544,046).

BACKGROUND OF THE INVENTION

The present invention relates to a new and distinct cultivar of *Lagerstroemia indica*. The new *Lagerstroemia* will hereafter by its cultivar name, 'Milaperl'. 'Milaperl' is a new cultivar of deciduous shrub grown for use as an ornamental landscape plant.

The new cultivar of *Lagerstroemia* is the result of a controlled breeding program conducted by the Inventor in Vertemate con Minoprio, Italy. 'Milaperl' originated as a seedling that arose from seeds that were pooled and sown in 1998 from open pollination of 33 unnamed and unpatented proprietary plants in the Inventor's breeding program, designated as breeding line No. 29.15. 'Milaperl' was selected as a single unique plant in 1999 from amongst the resulting seedlings. The exact parent plants are unknown.

Asexual propagation of the new cultivar was first accomplished by the Inventor using stem cuttings in 1999 in Vertemate con Minoprio, Italy. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Milaperl' as a unique cultivar of *Lagerstroemia.*

1. 'Milaperl' exhibits a well-branched plant habit.
2. 'Milaperl' exhibits an early and long lasting bloom period, flowering from early July through August in Northern Italy.
3. 'Milaperl' exhibits flowers that are pale pink in color.
4. 'Milaperl' exhibits good tolerance to powdery mildew.
5. 'Milaperl' exhibits good frost resistance; withstanding temperatures at least as low as −15° C.

'Milaperl' can be most closely compared to *Lagerstroemia indica* cultivars 'Milarosso', 'Milabla', 'Milarosa', and 'Milavio'. 'Milarosso' differs from 'Milaperl' in in having flowers that are dark pink in color. 'Milabla' differs from 'Milaperl' in having flowers that are white in color. 'Milarosa' differs from 'Milaperl' and in having flowers that mature to a deeper pink color. 'Milavio' differs from 'Milaperl' in having flowers that are violet in color.

BRIEF DESCRIPTION OF THE DRAWINGS

The accompanying colored photographs illustrate the overall appearance and distinct characteristics of the new *Lagerstroemia*. The photographs were taken of a plant two years in age as grown outdoors in a two-liter container in Zundert, The Netherlands.

The photograph in FIG. 1 provides a side view of 'Milaperl' in bloom.

Figure 1:
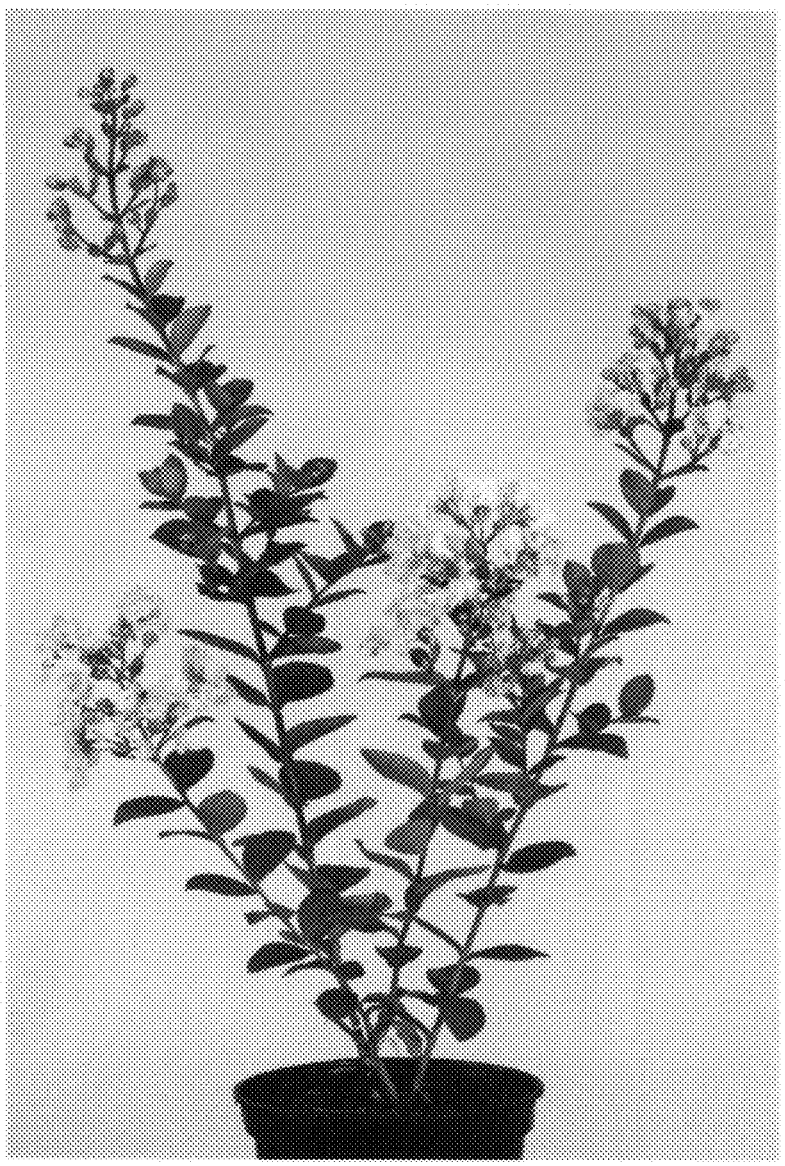
Figure 2:
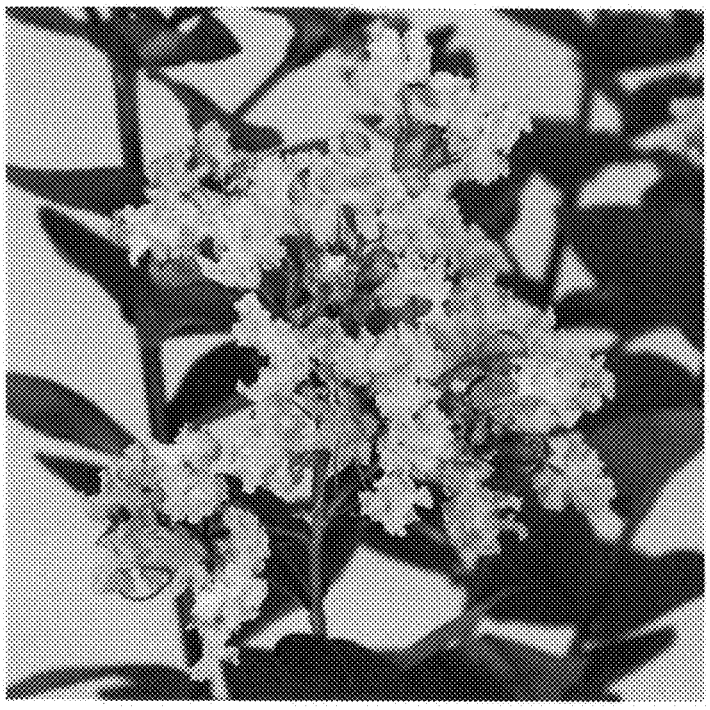

The photograph in FIG. 2 provides a close-up view of the inflorescences of 'Milaperl'.

Figure 3:
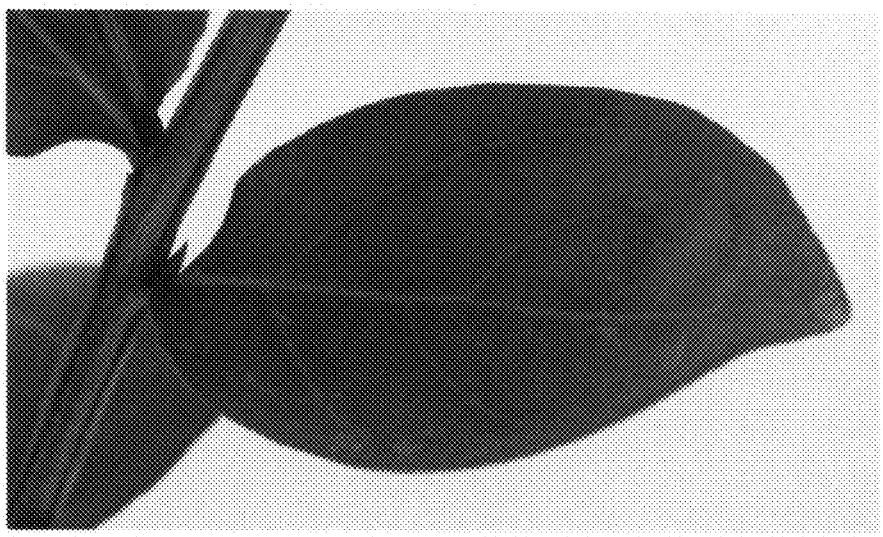

The photograph in FIG. 3 provides a close-up view of a leaf of 'Milaperl'.

The colors in the photographs are as close as possible with the digital photography techniques available, the color values cited in the detailed botanical description accurately describe the colors of the new *Lagerstroemia*.

DETAILED BOTANICAL DESCRIPTION

The descriptions were taken of plants two years in age as grown outdoors in 2-liter containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—From early July through August in Northern Italy.

*Plant type.*—Deciduous shrub.

*Plant habit.*—Upright and well-branched.

*Height and spread.*—An average of 61.2 cm in height and 35.5 cm in spread at two years of age in a 2-liter container.

*Cold hardiness.*—At least to U.S.D.A. Zone 8a.

*Diseases and pests.*—Good tolerance to powdery mildew caused by *Erysiphe lagerstroemia* has been observed.

*Root description.*—Fibrous and fine.

*Root development.*—Roots in 6 weeks and fully develops in a 9-cm container in about 4 months.

*Propagation.*—Stem cuttings.

*Growth rate.*—Moderate.

Stem description:

*Shape.*—Quadrangulate with rounded wings.

*Stem color.*—A blend of 174B and 177B with wings N170A.

*Stem size.*—An average of 33.9 cm in length and 2.9 mm in diameter.

*Stem surface.*—Slightly glossy.

*Stem strength.*—Strong.

*Branching.*—An average of 4 lateral branches, freely branching.

*Internode length.*—An average of 2.9 cm.

Foliage description:

*Leaf shape.*—Elliptic.

*Leaf division.*—Single.

*Leaf base.*—Attenuate.

*Leaf apex.*—Acute to broadly acute.

*Leaf venation.*—Pinnate, color; upper surface 144C and lower surface 147D.

*Leaf margins.*—Entire.

*Leaf arrangement.*—Opposite to nearly opposite.

*Leaf attachment.*—Petiolate.

*Leaf surface.*—Both surfaces glabrous.

*Leaf size.*—An average of 5.0 cm in length and 3.3 cm in width.

*Leaf quantity.*—An average of 24 (12 pairs) per branch.

*Leaf color.*—Young and mature leaves upper surface; 143A, young leaves lower surface; 146D, mature growth lower surface; a blend between 145A and 146D.

*Leaf fragrance.*—Fragrance typical for *Lagerstroemia* detected when touched.

*Petioles.*—An average of 1 mm in length and width, 147D in color, slightly glossy surface.

Flower description:

*Inflorescence type.*—Terminal thyrse.

*Lastingness of inflorescence.*—About one week.

*Inflorescence size.*—An average of 11.1 cm in height and 10.8 cm in width.

*Inflorescence number.*—An average of 7 per lateral stem.

*Flower number.*—An average of 49 flowers per inflorescence.

*Flower fragrance.*—Very faint sweet scent.

*Flower buds.*—Broadly obovate in shape, an average of 9 mm in diameter and 8 mm in depth, rounded apex, surface; glabrous, color; 145B with margins of immature sepals 174B.

*Flower aspect.*—Upright to outward.

*Flower type.*—Rotate.

*Flower size.*—An average of 4.6 cm in diameter and 2.6 mm in depth.

*Petals.*—An average of 6, rotate in arrangement, reniform in shape, strongly undulate bidentate margins, stalked base, praemorse apex, both surfaces glabrous and dull, an average of 2.0 cm in length and 1.5 cm in width, color when opening and when fully open upper and lower surface; 75B with stalk 64B, petal color does not fade.

*Calyx.*—Rotate in shape, an average of 1.2 cm in length and 1.6 cm in diameter.

*Sepals.*—An average of 6 petals, rotate arrangement, fused at base, rhomboidal in shape, entire margins, acuminate apex, both surfaces smooth and dull, an average of 1.2 cm in length and 4 mm in width, color; upper surface when opening and when fully open 145B, lower surface when opening and when fully open 144B to 144C.

*Peduncles.*—Strong, an average of 9.3 cm in length and 0.3 mm in width, 181A in color, surface is slightly glossy, main peduncles held at an average angle of 0° to the lateral branch, secondary peduncles held at an average angle of 55° to the lateral branch.

*Pedicels.*—Strong, an average of 1.6 cm in length and 1 mm in width, 143B to 143C tinged with 174B to 174C in color, surface is slightly glossy, main pedicels held at an average angle of 0° to the lateral branch, secondary pedicels held at an average angle of 30° to the lateral branch.

Reproductive organs:

*Stamens.*—Average of 40, anther; an average of 2 mm in length, dorsifixed, narrow oblong in shape, 165B in color, filament; an average of 1.3 cm in length and 157D in color, pollen is moderate in quantity and 9B in color.

*Pistils.*—An average of 1, an average of 2 cm in length, style; an average of 1.9 cm in length and 146C to 146D in color, stigma is club-shaped and 146A in color, ovary is 151D in color.

*Seed and fruit.*—None observed.

It is claimed:

1. A new and distinct cultivar of *Lagerstroemia* plant named 'Milaperl' as herein illustrated and described.

* * * * *